United States Patent
Xu et al.

(10) Patent No.: US 7,345,214 B2
(45) Date of Patent: Mar. 18, 2008

(54) MODIFIED PT/RU CATALYST FOR RING OPENING AND PROCESS USING THE CATALYST

(75) Inventors: Feng Xu, Buffalo Grove, IL (US); Lorenz J. Bauer, Schaumburg, IL (US); Ralph D. Gillespie, Gurnee, IL (US); Maureen L. Bricker, Buffalo Grove, IL (US); Steven A. Bradley, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 16 days.

(21) Appl. No.: 11/242,560

(22) Filed: Oct. 3, 2005

(65) Prior Publication Data

US 2007/0078289 A1    Apr. 5, 2007

(51) Int. Cl.
*C07C 4/02* (2006.01)
*B01J 23/00* (2006.01)
*B01J 23/42* (2006.01)
*B01J 21/00* (2006.01)
*B01J 20/00* (2006.01)

(52) U.S. Cl. ............ 585/752; 502/258; 502/261; 502/262; 502/302; 502/303; 502/304; 502/313; 502/314; 502/326; 502/327; 502/332; 502/334; 502/339; 502/349; 502/350; 502/351; 502/355; 502/415; 502/439

(58) Field of Classification Search .......... 502/258, 502/261, 262, 302–304, 313, 326, 327, 332, 502/334, 339, 349, 350, 351, 355, 415, 439
See application file for complete search history.

(56) References Cited

U.S. PATENT DOCUMENTS

| | | | | |
|---|---|---|---|---|
| 2,953,455 A * | 9/1960 | Maffet | ............ | 430/608 |
| 3,183,278 A * | 5/1965 | Koch, Jr. | ............ | 585/268 |
| 3,554,929 A * | 1/1971 | Aarons | ............ | 502/178 |
| 3,617,511 A | 11/1971 | Jenkins et al. | ............ | 208/112 |
| 3,723,078 A * | 3/1973 | Parker | ............ | 428/559 |
| 3,759,841 A * | 9/1973 | Wilhelm | ............ | 502/227 |
| 3,806,447 A | 4/1974 | Hayes | ............ | 208/139 |
| 5,345,026 A | 9/1994 | Chang et al. | ............ | 585/700 |
| 5,382,730 A | 1/1995 | Breckenridge et al. | ..... | 585/310 |
| 5,463,155 A | 10/1995 | Galperin et al. | ............ | 585/310 |
| 5,811,624 A | 9/1998 | Hantzer et al. | ............ | 585/700 |
| 6,235,962 B1 * | 5/2001 | Zeuthen | ............ | 585/700 |
| 6,241,876 B1 | 6/2001 | Tsao et al. | ............ | 208/137 |
| 6,551,960 B1 * | 4/2003 | Laine et al. | ............ | 502/327 |
| 2002/0040175 A1 | 4/2002 | Baird, Jr. et al. | ............ | 585/700 |
| 2002/0043481 A1 | 4/2002 | Baird, Jr. et al. | ............ | 208/137 |
| 2002/0050466 A1 | 5/2002 | Baird, Jr. et al. | ............ | 208/137 |

(Continued)

FOREIGN PATENT DOCUMENTS

EP    0 875 288 A1    11/1998

*Primary Examiner*—Cam N. Nguyen
(74) *Attorney, Agent, or Firm*—Frank S Molinaro

(57) ABSTRACT

A catalyst for opening naphthenic rings has been developed. The catalyst comprises ruthenium and platinum as the active catalytic metals and a modifier with cerium being a preferred modifier. At least 50% of the platinum and ruthenium components are present as particles wherein more ruthenium is present on the surface of the particles than in the center. All of these components are dispersed on a metal oxide support such as aluminas. A ring opening process using the catalyst is also described.

21 Claims, 1 Drawing Sheet

U.S. PATENT DOCUMENTS

| | | | |
|---|---|---|---|
| 2002/0063082 A1 | 5/2002 | Touvelle et al. | 208/134 |
| 2004/0204504 A1* | 10/2004 | Malek et al. | 518/717 |
| 2005/0101474 A1 | 5/2005 | Galperin et al. | 502/64 |
| 2005/0101819 A1 | 5/2005 | Galperin et al. | 585/752 |
| 2005/0131255 A1* | 6/2005 | Benderly et al. | 562/546 |
| 2007/0031722 A1* | 2/2007 | Adzic et al. | 429/44 |

* cited by examiner

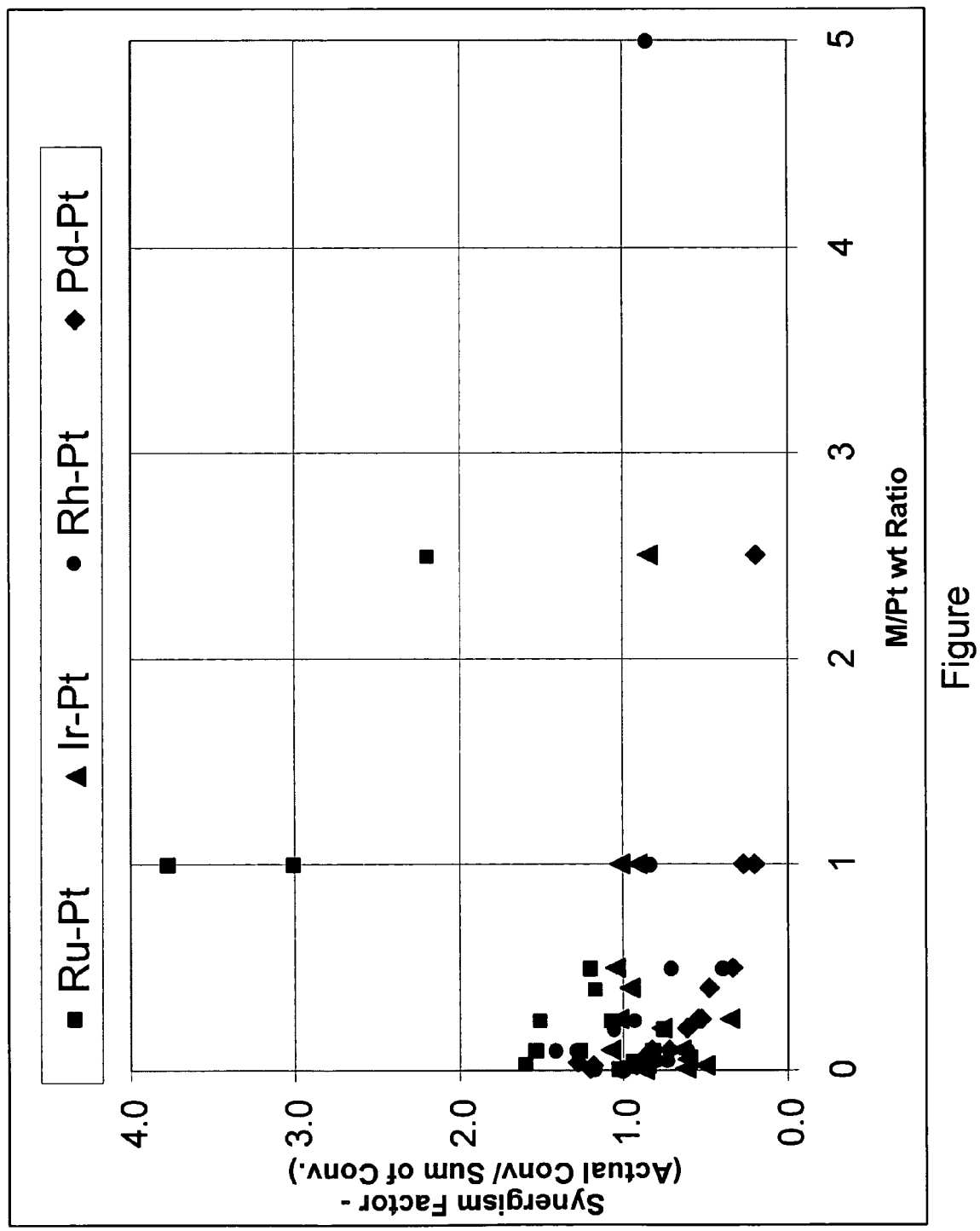
Figure

MODIFIED PT/RU CATALYST FOR RING OPENING AND PROCESS USING THE CATALYST

FIELD OF THE INVENTION

This invention relates to a catalyst effective for opening naphthenic rings. The catalyst comprises a platinum component, a ruthenium component, and a modifier component all dispersed on a refractory inorganic oxide. A fraction of the platinum and ruthenium components are present as particles where the surface of the particles is enriched with ruthenium. The invention also relates to a ring opening process using the catalyst.

BACKGROUND OF THE INVENTION

There is an increasing demand for clean burning high performance fuels. Distillate fuels, e.g. straight-run light naphtha, typically contain paraffins, naphthenes and aromatics. Naphthenes, i.e. cyclic paraffins, such as methylcyclopentane (MCP) and cyclohexane (CH) have low octane numbers (RON) of 91 and 83, respectively. If the rings are opened and isomerized, the resulting isomerized paraffins have higher octane numbers. Paraffins also have a lower density than the corresponding naphthenes. Thus, there is a need for improved catalysts for ring opening.

An increased amount of paraffins is also required in providing reformulated gasoline. Reformulated gasoline differs from the traditional product in having a lower vapor pressure, lower final boiling point, increased content of oxygenates, and lower content of olefins, benzene and aromatics.

Reduction in gasoline benzene content often has been addressed by changing the cut point between light and heavy naphtha and directing more of the potential benzene formers to isomerization instead of to reforming. No benzene is formed in isomerization, wherein benzene is converted to $C_6$ naphthenes and $C_6$ naphthenes are isomerized toward an equilibrium mixture of cyclohexane and methylcyclopentane or converted to paraffins through ring opening. It is believed that such $C_6$ cyclics are preferentially adsorbed on catalyst sites relative to paraffins, and the cyclics thus have a significant effect on catalyst activity for isomerization of paraffins. Refiners thus face the problem of maintaining the performance of light-naphtha isomerization units which process an increased concentration of feedstock cyclics.

Ring opening is the preferred reaction to improve the paraffin content of feedstreams to isomerization units because ring opening involves cleaving of only one carbon-carbon bond on the ring(s) while maintaining the same number of carbon atoms as the starting molecule. Hydrogenolysis on the other hand involves breaking one or more carbon-carbon bonds, while cracking involves cleavage of more than one carbon-carbon bond to form molecules of lower carbon number. For this application it is very desirable to use a catalyst which has high activity and selectivity to ring opening at relatively low temperatures of about 125° C. to 250° C.

Catalysts which are useful for ring opening are known and include a high chloride platinum component dispersed on a refractory inorganic oxide which is described in U.S. Pat. No. 5,463,155. U.S. Pat. No. 5,811,624 describes a catalyst for the selective opening of 5 and 6 membered rings which consists of a transition metal catalyst selected from the group consisting of carbides, nitrides, oxycarbides, oxynitrides, and oxycarbonitrides. The transition metal is selected from the group consisting of metals from Group IVA, VA, VIA of the Periodic Table of the Elements. U.S. Pat. No. 6,235,962 B1 discloses a catalyst for ring opening which comprises a carrier consisting of alumina, a metal modifier selected from the group consisting of scandium, yttrium and lanthanum, and at least one catalytically active metal selected from the group consisting of platinum, palladium, rhodium, rhenium, iridium, ruthenium, and cobalt. U.S. Pat. No. 5,382,730 discloses a process for ring opening and isomerization of hydrocarbons where the catalyst comprises an aluminosilicate zeolite such as Zeolite Y or Zeolite Beta and a hydrogenation component. U.S. Pat. No. 5,345,026 discloses a process for conversion of cyclic hydrocarbons to non-cyclic paraffin hydrocarbons where the catalyst comprises a hydrogenation-dehydrogenation component and an acidic solid component comprising a group IVB metal oxide modified with an oxyanion of a group VIB metal. U.S. Pat. No. 3,617,511 discloses a catalyst for conversion of cyclic hydrocarbons to paraffins where the catalyst comprises rhodium or ruthenium on a halogen promoted refractory oxide. U.S. Pat. No. 6,241,876 discloses a ring opening catalyst which comprises a large pore crystalline molecular sieve component with a faujasite structure and an alpha acidity of less than one and a Group VIII noble metal. US Publication No. 2002/43481 A1 discloses a catalyst for naphthene ring opening which comprises at least one Group VIII metal selected from iridium, platinum, rhodium and ruthenium on a refractory inorganic oxide substrate containing at least one of an alkali metal and alkaline earth metal. US Publication No. 2002/40175 A1 discloses a naphthene ring opening catalyst comprising a Group VIII metal selected from iridium, platinum, palladium, rhodium, ruthenium and combinations thereof. With the metal being supported on the substrate comprising at least one of a Group IB, IIB, and IVA metal. US Publication No. 2002/50466 A1 discloses a naphthenic ring opening catalyst comprising iridium in combination with at least one of platinum, rhodium and ruthenium. Finally, US Publication No. 2002/63082 A1 discloses a process where a naphtha feed is first contacted with a ring opening catalyst containing a Group VIII metal and then taking the product and contacting it with a cracking catalyst.

Applicants have developed a catalyst comprising platinum, ruthenium and a modifier such as cerium or rhenium dispersed on a refractory inorganic oxide support. Applicants have discovered that combining ruthenium with platinum results in a synergistic effect, which effect can be enhanced by addition of a modifier component. The catalyst is further characterized in that at least 50% of the platinum and ruthenium components are present as particles where the surface of the particles are enriched in ruthenium versus the center of the particles.

SUMMARY OF THE INVENTION

As stated, this invention relates to a catalyst for opening naphthenic rings and a process using the catalyst. Accordingly, one embodiment of the invention is a catalyst for opening naphthenic rings comprising a platinum component, a ruthenium component and a modifier component all dispersed on a refractory inorganic oxide support characterized in that at least 50% of the platinum and ruthenium components are present as particles wherein the surface of the particles has a higher concentration of ruthenium than the center of the particles.

Another embodiment of the invention is a process for producing acyclic paraffins from cyclic paraffins comprising contacting a feed stream comprising cyclic paraffins with a catalyst comprising a platinum component, a ruthenium component and a modifier component all dispersed on a refractory inorganic oxide support at ring opening conditions to convert at least a portion of the cyclic paraffins to acyclic paraffins. The catalyst characterized in that at least 50% of the platinum and ruthenium components are present as particles wherein the surface of the particles has a higher concentration of ruthenium than the center of the particles.

These and other objects and embodiments will become clearer after a detailed description of the invention.

BRIEF DESCRIPTION OF THE DRAWING

The FIGURE presents a plot of Synergism Factor versus M/Pt wt. ratios as set forth in Example 8.

DETAILED DESCRIPTION OF THE INVENTION

One essential element of the catalyst of the present invention is a support which comprises a refractory inorganic oxide. Inorganic oxides which can be used are any of those well known in the art and include but are not limited to aluminas, silica/alumina, silica, titania, calcium oxide, magnesium oxide, clays and zirconia. In order to avoid confusion it is pointed out that the term silica/alumina does not mean a physical mixture of silica and alumina but means an acidic and amorphous material that has been cogelled or coprecipitated. The term is well known in the art, see e.g. U.S. Pat. No. 3,909,450; U.S. Pat. No. 3,274,124 and U.S. Pat. No. 4,988,659. The aluminas which can be used include gamma alumina, theta alumina, delta and alpha alumina.

Although the supports can be used as powders it is preferred to form the powder into shaped articles. Examples of shaped articles include but are not limited to spheres, pills, extrudates, irregularly shaped particles and tablets. Methods of forming these various articles are well known in the art.

Spherical particles may be formed, for example, from the preferred alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to a gamma-alumina support by known methods; (2) forming an extrudate from the powder by established methods and thereafter rolling the extrudate particles on a spinning disk until spherical particles are formed which can then be dried and calcined to form the desired particles of spherical support; and (3) wetting the powder with a suitable peptizing agent and thereafter rolling the particles of the powder into spherical masses of the desired size.

Instead of peptizing an alumina powder, spheres can be prepared as described in U.S. Pat. No. 2,620,314 which is incorporated by reference in its entirety. The first step in this method involves forming an aluminum hydrosol by any of the techniques taught in the art and preferably by reacting aluminum metal with hydrochloric acid. The resultant hydrosol is combined with a suitable gelling agent such as hexamethylene tetraamine (HMT). The resultant mixture is dropped into an oil bath which is maintained at a temperature of about 90° C. to about 100° C. The droplets of the mixture remain in the oil bath until they set and form hydrogel spheres. Next the spheres are continuously withdrawn from the oil bath and treated with an ammoniacal solution at a temperature of about 80° C. to about 95° C. for a time of about 2 to about 2.5 hours. After treatment with the ammoniacal solution, the spheres are dried at a temperature of about 80° C. to about 150° C. and then calcined at a temperature of about 400° C. to about 700° C. for a time of about 1 to about 24 hours.

Extrudates are prepared by mixing the inorganic oxide with water and suitable peptizing agents such as nitric acid, acetic acid, etc. until an extrudable dough is formed. The resulting dough is then extruded through a suitably sized die to form extrudate particles. The extrudate particles are dried at a temperature of about 150° C. to about 200° C. and then calcined at a temperature of about 450° C. to 800° C. for a period of about 0.5 to about 10 hours to effect the preferred form of the refractory inorganic oxide.

On the support are dispersed a platinum component, a ruthenium component and a modifier component. The platinum and ruthenium components can be deposited on the inorganic oxide by means well known in the art such as spray impregnation or evaporative impregnation. Both spray or evaporative impregnation use a solution containing a decomposable compound of the desired metal. By decomposable is meant that upon heating the compound decomposes to provide the catalytic form of platinum and ruthenium component. Non-limiting examples of decomposable compounds which can be used include chloroplatinic acid, ammonium chloroplatinate, platinum tetrachloride hydrate, tetraamine platinum chloride, platinum nitrate, ruthenium tetrachloride, ruthenium nitrate, ruthenium trichloride, hexaamine ruthenium chloride, ruthenium nitrosyl chloride, ruthenium nitrosyl nitrate, ruthenium red hydrate, ammonium hexachlororuthenate(IV), ruthenocene and triruthenium dodecacarbonyl. The solvent which is used to prepare the solution is usually water although organic solvents such as alcohols, dimethyl formamide (DMF), dimethylsulfoxide (DMSO), tetrahydrofuran (THF) and amines, e.g., pyridine can be used.

Spray impregnation involves taking a small volume of the solution and spraying it over the support while the support is moving. When the spraying is over, the wetted support can be transferred to other apparatus for drying or finishing steps.

One particular method of evaporative impregnation involves the use of a steam-jacketed rotary dryer. In this method the support is immersed in the impregnating solution which has been placed in the dryer and the support is tumbled by the rotating motion of the dryer. Evaporation of the solution in contact with the tumbling support is expedited by applying steam to the dryer jacket. The impregnated support is then dried at a temperature of about 60° C. to about 150° C. and then reduced at a temperature of about 300° C. to about 850° C. for a time of about 30 minutes to about 8 hours to give the catalyst.

The final form of the platinum and/or ruthenium component on the support can be the metal, oxide, sulfide, halide or oxyhalide with the metal, i.e. reduced state, being the usual case. The amount of platinum and ruthenium present on the catalyst can vary widely, but is usually for platinum from about 0.05 to about 10 wt. % of the catalyst as the metal and for ruthenium from about 0.05 to about 10 wt. % of the catalyst as the metal. The amount of modifier component is present in an amount from about 0.5 to about 10 wt. % of the catalyst as the element.

It is also desirable that the platinum and ruthenium metals be mostly present as particles containing both components. More specifically, it is desirable that at least 50%, preferably at least 70% and most preferably at least 80% of the platinum and ruthenium components be present as particles containing atoms of both components. These particles are further characterized in that the surface of the particles contains a higher concentration of ruthenium than the center of the particles. It is desirable that the surface contain at least 10 atomic % more, preferably at least 20 atomic % more and most preferably at least 30 atomic % more ruthenium.

As will be shown in the examples, there is a synergistic effect between ruthenium and platinum. In this respect, a synergism factor can be calculated using the following equation:

$$SF = \text{Actual Conv.}/\text{Sum of Individual Conv.}$$

where SF is the synergism factor. For the Pt/Ru systems, a considerable number of the formulations tested have a large SF. Accordingly, it is desirable to have a catalyst containing platinum and ruthenium with an SF of at least 1.5.

Another component of the catalyst of the invention is a modifier component. Generally, the modifier component can be a Group VIII (IUPAC Groups 8-10) metal of the Periodic Table of the Elements, a rare earth element or an element from Groups VIB, VIIB, IIIA, IVA or mixtures thereof. Examples of modifiers include but are not limited to rhenium, molybdenum, tungsten, tin, germanium, cerium, yttrium, praeseodymium, ytterbium, and thulium, with cerium being especially preferred. The modifier component is deposited onto the support in the same manner as for the platinum and/or ruthenium component described above. Non-limiting examples of decomposable compounds include perrhenic acid, tin chloride, ammonium heptamolybdate, ammonium metatungstate, germanium chloride, cerium nitrate, yttrium chloride, praseodymium chloride, ytterbium chloride, and thulium nitrate.

The platinum, ruthenium and modifier components can be deposited onto the support individually in any order or combined in any combination although not necessarily with equivalent results. It is preferred that the modifier be deposited onto the support prior to the deposition of platinum and ruthenium with an intermediate calcination step. In some cases, modifier, platinum and ruthenium compounds can be deposited onto the support in one step. An acid such as hydrochloric acid can optionally be added to moderate the adsorption of the platinum and ruthenium compounds onto the support. After impregnating with Ru and Pt, the catalyst is dried at a temperature of about 60° C. to about 120° C. Further treatment in air, hydrogen or nitrogen, either under dry or ambient humidity is optional. These treatments are carried out at temperatures of about 100° C. to about 550° C. for a time of about 1 to about 8 hours. A reduction step, either after drying or after drying and the optional treatment step, in hydrogen is required to generate the reduced catalyst. Reduction is carried out at a temperature of about 300° C. to about 850° C. for a time of about 30 minutes to about 8 hours.

The catalyst described above is used in a process where cyclic paraffins are opened or cleaved to acyclic paraffins. The feeds which can be used in the ring opening process are any of those which comprise $C_5$-$C_6$ aliphatic rings, i.e. naphthenic rings. Naphtha feeds usually comprise aromatic, naphthene and paraffin components. Feed stocks which may be utilized include straight-run naphthas, natural gasoline, synthetic naphthas, thermal gasoline, catalytically cracked gasoline, partially reformed naphthas or raffinates from extraction of aromatics. The feedstock essentially is encompassed by the boiling range of a full range naphtha, or within the range of 0° C. to 230° C. Usually the feedstock is light naphtha having an initial boiling point of about 10° C. to 65° C. and a final boiling point from about 75° C. to 110° C.; preferably, the final boiling point is less than about 95° C.

The amount of aromatic, naphthene and paraffin components present in the feedstock can vary substantially but usually aromatics are present from about 0.1 to 20 wt. %, naphthenes from about 1 to 35 wt. % and paraffins from about 45 to 95 wt. %.

The feedstream is contacted with the catalyst at ring opening conditions which include a temperature of about 120° C. to about 300° C., a pressure of about $9.87 \times 10^1$ kPa (14.3 psi) to about $6.89 \times 10^3$ kPa, (1000 psi) and preferably from about $1.03 \times 10^3$ kPa (150 psi) to about $3.10 \times 10^3$ kPa (450 psi), a liquid hourly space velocity of about 0.25 to about 10 hr$^{-1}$ and preferably about 0.5 to about 2 hr$^{-1}$ and $H_2$/HC (hydrocarbon) mole ratio from about 0.5 to about 5.

The following examples are presented in illustration of this invention and are not intended as undue limitations on the generally broad scope of the invention as set out in the appended claims.

EXAMPLE 1

Into a rotary evaporator there were added 53 grams of HCl (5.5% HCl) solution, 50 grams chloroplatinic acid solution (0.99% Pt), 145 grams of $RuCl_3$ solution (0.39% Ru) and 100 g of θ-alumina spheres. The resulting mixture was rolled at ambient conditions for one hour, followed by the application of steam for another hour to remove the water and then cooled to room temperature. These catalysts were found to contain 0.43% Ru and 0.39% Pt. This catalyst was identified as catalyst A. The resulting catalyst was crushed to 40-60 mesh and then treated under various conditions as set forth in Table 1.

Samples of the catalysts after each treatment condition were tested for ring opening activity as follows. About 35 mg was placed in a fixed bed reactor and reduced under hydrogen for 4 hours at 450° C. Next the temperature was lowered to 200° C. and a hydrogen/methylcyclopentane (35:1 mole ratio) was flowed through the catalyst bed at a weight hourly gas velocity (WHSV) of 0.5 hr.$^{-1}$ and the effluent analyzed by online gas chromatography. The results are presented in Table 1 along with a reference catalyst prepared as above but containing only 0.37% Pt dispersed on gamma alumina.

TABLE 1

Effect of Treatment Conditions on Pt/Ru Catalysts

| Sample ID | Calc Temp °C. | Time | Gas Flow | Humidity | Conversion (%) | Ring opening (%) | Cyclohexane (%) | Cracking C1-C5 (%) |
|---|---|---|---|---|---|---|---|---|
| A-1 | 150 | 4 h | air, STATIC | ambient | 73 | 86 | 0 | 14 |
| A-2 | 200 | 4 h | air, STATIC | ambient | 65 | 86 | 0 | 13 |
| A-3 | 350 | 4 h | air, STATIC | ambient | 8 | 69 | 1 | 30 |
| A-4 | 250 | 4 h | air, 1 lpm | dry | 50 | 87 | 0 | 12 |
| A-5 | 200 | 4 h | $N_2$, 1 lpm | dry | 76 | 85 | 0 | 14 |
| A-6 | 250 | 4 h | $N_2$, 1 lpm | dry | 84 | 83 | 0 | 16 |
| A-7 | 300 | 4 h | $N_2$, 1 lpm | dry | 66 | 86 | 0 | 13 |
| A-8 | 450 | 2 h | $H_2$ | dry | 86 | 83 | 0 | 16 |
| Ref | 150 | 4 h | air, static | dry | 0 | — | — | — |

The results indicate that for best conversion and selectivity catalyst A should be calcined in air at a temperature between about 150° C. and about 200° C., or heated under nitrogen at about 210° C. to about 250° C. The best conversion, i.e. highest activity was obtained after heating under hydrogen at about 450° C. It is also noted that a platinum only catalyst has no activity under these conditions.

EXAMPLE 2

Into a rotary evaporator there were added 25 g of an HCl solution (10% HCl) and 17.3 g of chloroplatinic acid solution (0.99% Pt). To this mixture there were added 50 g of θ-alumina spheres followed by 30.2 g of ruthenium red solution (0.51% Ru). The impregnated spheres were rolled at ambient conditions for one hour and then heated with steam for about an hour to remove the water. This catalyst was found to have 0.29% Pt and 0.32% Ru and identified as catalyst B.

The above spherical catalyst was crushed to 40-60 mesh particles and then treated under various conditions as described in Table 2. After treatment, samples of the catalyst were tested as in Example 1 and the results presented in Table 2.

sample B-4, it is observed that catalysts prepared with $RuCl_3$ are more active than those prepared using ruthenium red.

EXAMPLE 3

Trimetallic ring opening catalysts with different modifiers were prepared starting with 40-60 mesh gamma alumina particles. Approximately 300 mg of support was placed in discrete wells. Modifier metal salts were dissolved in water, and solutions were added to the wells. The mixture was agitated for half an hour, dried in air at 80-100° C., and then calcined in a muffle oven at 350° C. in air for 4 hours. Ruthenium chloride and chloroplatinic acid were pipetted into wells containing the calcined supports. Hydrochloric acid also was added to some wells. After brief agitation and drying, the catalysts were loaded into a high-throughput micro-reactor system for reduction and ring opening catalytic tests. The dried catalysts were reduced and tested as in example 1. No other treatments were done before the catalysts were reduced. Samples were also prepared without

TABLE 2

Ring Opening Activity of Various Catalysts

| Sample ID | Calc Temp °C. | Time | Gas Flow | Humidity | Conversion | Ring opening | Cyclohexane | Cracking |
|---|---|---|---|---|---|---|---|---|
| B-1 | Dried only | 1 h | Static | dry | 34 | 87 | 0 | 13 |
| B-2 | 350 | 4 h | air, Static | ambient | 3 | 72 | 2 | 28 |
| B-3 | 250 | 4 h | air, 0.12 lpm | dry | 40 | 87 | 0 | 12 |
| B-4 | 450 | 2 h | $H_2$ | dry | 47 | 85 | 0 | 15 |

Comparing the results of Table 1 and Table 2, specifically sample A-3 versus sample B-2, and sample A-8 versus sample B-4, it is observed that catalysts prepared with modifiers. A description of these samples along with the test results are presented in Table 3.

TABLE 3

Effect of Modifiers on Ring Opening Activity

| Ru wt % | Pt wt % | Modifier | Modifier Level wt % | HCl wt % | Conversion | Ring opening | Cyclohexane | Cracking |
|---|---|---|---|---|---|---|---|---|
| 0.5 | 0.25 | None | 0 | 0 | 31 | 92 | 1 | 9 |
| 0.5 | 0.25 | None | 0 | 1.5 | 33 | 92 | 1 | 9 |
| 0.5 | 0.25 | Ce | 0.2 | 1.5 | 61 | 88 | 0 | 13 |

TABLE 3-continued

Effect of Modifiers on Ring Opening Activity

| Ru wt % | Pt wt % | Modifier | Modifier Level wt % | HCl wt % | Conversion | Ring opening | Cyclohexane | Cracking |
|---|---|---|---|---|---|---|---|---|
| 0.5 | 0.25 | Ce | 1 | 1.5 | 73 | 86 | 0 | 15 |
| 0.5 | 0.25 | Pd | 0.2 | 1 | 19 | 94 | 2 | 7 |
| 0.5 | 0.25 | Re | 0.2 | 1.5 | 32 | 92 | 1 | 9 |
| 0.5 | 0.25 | Sn | 1 | 1 | 4 | 97 | 10 | 7 |
| 0.5 | 0.25 | Yb | 1 | 1.5 | 47 | 91 | 1 | 9 |

The results in Table 3 indicate that under these conditions and methods of preparation, cerium and ytterbium are preferred modifiers.

EXAMPLE 4

In a rotary evaporator, 30 grams of $CeCl_3$ (5.3% Ce) solution and 165 grams of water were added, followed by 110 g of spherical gamma-alumina. The impregnated spheres were rolled at ambient conditions for one hour, and then heated with steam for an additional hour to remove the water. After cooling to room temperature, the resulting supports were calcined in a muffle oven at different temperatures. The various Ce/gamma alumina supports were impregnated with RuCl3 and chloroplatinic acid as in Example 1. The dried catalysts were then crushed and approximately 35 mg of 40-60 mesh catalysts were loaded in the micro reactors for testing. The reduction and testing procedures were the same as described in Example 1. For comparison, a reference Ru/Pt/gamma alumina catalyst was prepared and tested in the same manner. Table 4 presents a description of the catalysts and the test results.

The results in Table 4 indicate that it is preferred to have a calcinations step between the cerium, i.e. modifier impregnation and Pt/Ru impregnation. It is also preferred to calcine at a temperature of about 350° C. to about 750° C.

EXAMPLE 5

Re and Yb modified gamma supports were prepared as in Example 4. Ruthenium chloride and chloroplatinic acid were impregnated onto the modifier containing supports as in Example 4. Finally, they were reduced and tested as in Example 1. Table 5 presents a description of the catalysts as well as the results of the testing.

TABLE 4

Effect of Calcination Temperature on Ring Opening Activity

| Pt wt % | Ru wt % | Modifier | Modifier Level wt % | Calc Temp ° C. | Conversion | Ring opening | Cyclohexane | Cracking |
|---|---|---|---|---|---|---|---|---|
| 0 | 0 | Ce | 1.5 | Dry | 0 | 0 | 0 | 0 |
| 0.23 | 0.34 | Ce | 1.5 | Dry | 48 | 89 | 0 | 11 |
| 0.25 | 0.34 | Ce | 1.5 | 350 | 91 | 79 | 0 | 21 |
| 0.25 | 0.34 | Ce | 1.5 | 550 | 88 | 83 | 0 | 17 |
| 0.25 | 0.34 | Ce | 1.5 | 750 | 76 | 83 | 0 | 17 |
| 0.25 | 0.44 | NONE | 0 | Dry | 24 | 91 | 0 | 8 |

TABLE 5

Effect of Modifier and Calcination Conditions on Ring Opening Activity

| Pt wt % | Ru wt % | Modifier | Modifier Level wt % | Calc Temp ° C. | Conversion | Ring opening | Cyclohexane | Cracking |
|---|---|---|---|---|---|---|---|---|
| 0.22 | 0.31 | Re | 1.4 | Dry | 37 | 79 | 0 | 20 |
| 0.23 | 0.33 | Yb | 1.4 | Dry | 50 | 90 | 0 | 10 |
| 0.22 | 0.33 | Yb | 1.5 | 350 | 34 | 91 | 0 | 9 |
| 0.25 | 0.44 | NONE | 0 | Dry | 24 | 91 | 0 | 8 |

The results in Table 5 show that calcination is not necessary to achieve good activity for a Re or Yb containing catalyst.

EXAMPLE 6

Spherical gamma-alumina was crushed to 40-60 mesh particles which were then impregnated with an aqueous solution of cerium nitrate to give 3.5 wt. % Ce. The impregnated support was dried for six (6) hours at 150° C. and then calcined at 350° C. for two hours. Next the calcined cerium containing support was impregnated with an aqueous solution containing $RuCl_3$, chloroplatinic acid and HCl in sufficient amounts to give 0.25 wt. % Pt, 0.5 wt. % Ru and 1% Cl on the finished catalyst. The excess water was evaporated and the catalyst dried at 150° C. For 6 hours. This catalyst was identified as sample C.

Another catalyst was prepared by taking 40-60 mesh particles of the same gamma-alumina as above and impregnating it with water followed by drying at 150° C. and then calcining at 350° C. For two hours. This calcined support was impregnated as above to provide a catalyst with 0.25 wt. % Pt, 0.5 wt. % Ru and 1% Cl. This catalyst was identified as sample D.

The two catalysts were tested in a high pressure microreactor system as follows. The catalysts were reduced under flowing hydrogen at 450° C. For 4 hours. Next a feed comprising 30% methylcyclopentane (MCP), 15% cyclohexane, 50% heptane and 5% toluene. Hydrogen was added to give 4 moles of $H_2$ per mole of total hydrocarbons. The feed was flowed through the catalyst at a temperature of 250° C. and 350 psig. The catalysts were equilibrated for 40 hours and then tested at temperatures shown in Table 6.

TABLE 6

Effect of Cerium on Ring Opening Activity

| | Catalyst I.D. | | | |
|---|---|---|---|---|
| | C | C | C | D |
| Temp (C.) | 200 | 225 | 250 | 250 |
| Pressure (psig) | 350 | 350 | 350 | 350 |
| Time on stream | 60 | 80 | 40 | 40 |
| Molar Hydrogen/Hydrocarbon | 4 | 4 | 4 | 4 |
| WHSV (liquid) | 1 | 1 | 1 | 1 |
| MCP Conversion | 17.8 | 51.3 | 96.6 | 55.4 |
| Ring Opening Selectivity (%) | 84.6 | 75.3 | 45.8 | 68.7 |
| Product Yields (wt %) | | | | |
| C4- | 0.4 | 2.7 | 24.2 | 4.8 |
| C5 | 0.4 | 2.5 | 14.2 | 3.3 |
| C6 paraffin | 4.7 | 16.0 | 32.6 | 17.9 |
| Methylcyclopentane | 24.9 | 14.8 | 1.0 | 13.5 |
| Cyclohexane | 14.2 | 12.5 | 3.2 | 11.7 |
| Methylcyclohexane | 5.3 | 4.9 | 1.7 | 4.6 |
| Heptane | 49.9 | 46.7 | 22.8 | 44.1 |
| Toluene | 0.0 | 0.0 | 0.0 | 0.0 |

The results of Table 6 show that the addition of cerium improves both activity and selectivity for ring opening even at temperatures as low as 200° C.

EXAMPLE 7

In a rotary evaporator 6.2 g of Ce $(NO_3)_2.6H_2O$ were dissolved in 800 ml of deionized water. To this solution there were added 400 ml of 1.6 mm (1/16 inch) diameter gamma alumina spheres. The resulting mixture was rolled at ambient temperature for one hour and then heated with steam for another hour to remove the water. After cooling to room temperature, the resulting impregnated support was calcined in a muffle oven at 350° C. For 6 hours. The calcined Ce containing spheres were impregnated with ruthenium and platinum as set forth in Example 1 and then reduced in hydrogen at 450° C. For 4 hours. Analysis of the finished catalyst showed that it contained 0.75 wt. % Re, 0.5 wt. % Pt and 1 wt. % Ce.

The catalyst prepared above was analyzed using Scanning Transition Electron Microscopy (STEM) to determine particle sizes and Pt and Ru metal distribution. STEM analysis showed that the average particle or cluster size was about 8.6 Å. Further analysis of clusters of 20 to 30 Å showed that the surface of the clusters was ruthenium enriched.

EXAMPLE 8

A series of catalysts were prepared and tested to determine the synergism between catalytic metals. Catalysts were prepared containing the following metals: Pt only; Pd only; Ir only; Ru only; Rh only; Pt—Pd; Pt—Ru; Pt—Ir and Pt—Rh. The catalysts were prepared by placing 300 mg of theta alumina (40-60mesh) into each of 48 wells of a reaction plate. To each well there was added deionized water. Next, the desired aqueous metal solution was added. Individual solutions containing $H_2PtCl_6$, $PdCl_2$, ruthenium red, $RhCl_3$ or $H_2IrCl_6$ were used. In the case of bimetal compositions, the $H_2PtCl_6$ solution was added first, followed by the second metal solution. The total amount of volume of solution added to each well was kept constant at 650 microliter. After all the wells were filled with solution, the plate was sealed and then shaken on a mechanical shaker at 60 rpm for 15 minutes before air was flowed over each well to remove the water. After further drying at 120° C. For 6 hours, the samples were then calcined in a muffle oven at 350° C. For 6 hours.

The samples were tested per example 1 and a synergism factor (SF) was calculated as follows:

$SF$=Conversion of bimetallic catalyst/Sum of Conversion of each metal

The results of this testing are presented in the FIGURE where SF is plotted versus M/Pt wt. ratio. It is observed from the FIGURE that the Pt—Ru catalysts have the highest synergism, with most of these Pt/Ru catalysts having a SF>1.5.

We claim as our invention:

1. A catalyst for opening naphthenic rings comprising a platinum component, a ruthenium component and a modifier component all dispersed on a refractory inorganic oxide support and characterized in that at least 50% of the platinum and ruthenium components are present as particles, wherein the surface of the particles has a higher concentration of ruthenium than the center of the particles.

2. The catalyst of claim 1 wherein the modifier is selected from the group consisting of rare earth elements, rhenium, molybdenum, tungsten, tin, germanium and mixtures thereof.

3. The catalyst of claim 2 wherein the modifier is a rare earth element selected from the group consisting of cerium, ytterbium, praeseodymium, rhenium, thorium, thulium and mixtures thereof.

4. The catalyst of claim 1 wherein the refractory inorganic oxide support is selected from the group consisting of aluminas, silica, silica-alumina, zirconia, titania, and mixtures thereof.

5. The catalyst of claim 1 wherein the platinum component is present in an amount from about 0.05 to about 10 wt. % of the catalyst as the metal.

6. The catalyst of claim 1 wherein the ruthenium component is present in an amount from about 0.05 to about 10 wt. % of the catalyst as the metal.

7. The catalyst of claim 1 wherein the modifier component is present in an amount from about 0.1 to about 10 wt. % of the catalyst as the element.

8. The catalyst of claim 1 wherein the catalyst is in the form of a shaped article selected from the group consisting of pills, extrudates, spheres, irregularly shaped particles and tablets.

9. The catalyst of claim 1 wherein the particle surface contains at least 10 atomic % more ruthenium than the particle center.

10. The catalyst of claim 1 further characterized in that it has a synergism factor of at least 1.5.

11. A process for producing acyclic paraffins from cyclic paraffins comprising contacting a feed stream comprising cyclic paraffins with a catalyst, comprising a platinum component, a ruthenium component and a modifier component all dispersed on a refractory inorganic oxide support, at ring opening conditions to convert at least a portion of the cyclic paraffins to acyclic paraffins, the catalyst characterized in that at least 50% of the platinum and ruthenium components are present as particles wherein, the surface of the particles has a higher concentration of ruthenium than the center of the particles.

12. The process of claim 11 wherein the ring opening conditions include a temperature of about 120° C. to about 300° C., a pressure of about $1.03 \times 10^3$ to about $3.10 \times 10^3$ kPa, a liquid hourly space velocity of about 0.5 to about 2.0 $hr^{-1}$ and a $H_2$/HC (hydrocarbon) mole ratio from about 0.5 to about 5.

13. The process of claim 11 wherein the modifier is selected from the group consisting of rare earth elements, rhenium, molybdenum, tungsten, tin, germanium and mixtures thereof.

14. The process of claim 11 wherein the modifier is a rare earth element selected from the group consisting of cerium, ytterbium, thorium, thulium, praeseodymium and mixtures thereof.

15. The process of claim 11 wherein the modifier component is present in an amount from about 0.5 to about 10 wt. % of the catalyst as the element.

16. The process of claim 11 wherein the refractory inorganic oxide support is selected from the group consisting of aluminas, silica, silica-alumina, zirconia, titania and mixtures thereof.

17. The process of claim 11 wherein the platinum component is present in an amount from about 0.05 to about 10 wt. % of the catalyst as the metal.

18. The process of claim 11 wherein the ruthenium component is present in an amount from about 0.05 to about 10 wt. % of the catalyst as the metal.

19. The process of claim 11 wherein the catalyst is in the form of a shaped article selected from the group consisting of pills, extrudates, spheres, irregularly shaped particles and tablets.

20. The process of claim 11 wherein the particle surface contains at least 10 atomic % more ruthenium than the particle center.

21. The process of claim 11 wherein the catalyst is further characterized in that it has a synergism factor of at least 1.5.

* * * * *